(12) United States Patent
Zicherman

(10) Patent No.: US 6,196,990 B1
(45) Date of Patent: Mar. 6, 2001

(54) VIBRATOR APPLIANCE PARTICULARLY USEFUL FOR DIALYSIS

(76) Inventor: Yehuda Zicherman, 6 Yael Street, Beni Brak 51585 (IL)

(*) Notice: Subject to any disclaimer, the term of this patent is extended or adjusted under 35 U.S.C. 154(b) by 0 days.

(21) Appl. No.: 08/809,652

(22) PCT Filed: Jul. 24, 1996

(86) PCT No.: PCT/IL96/00064

§ 371 Date: Jul. 1, 1997

§ 102(e) Date: Jul. 1, 1997

(87) PCT Pub. No.: WO97/04820

PCT Pub. Date: Feb. 13, 1997

(30) Foreign Application Priority Data

Jul. 27, 1995 (IL) .......................................................... 114768

(51) Int. Cl.⁷ ..................................................... A61M 1/00

(52) U.S. Cl. .................................. 604/29; 61/49; 61/67; 61/71; 61/79

(58) Field of Search .......................... 604/22, 29; 601/46, 601/49–66, 48, 70, 71, 79, 84, 98, 103, 105, 151

(56) References Cited

U.S. PATENT DOCUMENTS

| | | |
|---|---|---|
| 1,147,560 * | 7/1915 | Shurtleff . |
| 2,118,699 * | 5/1938 | Chappell . |
| 2,492,671 * | 12/1949 | Wettlaufer . |
| 2,497,751 * | 2/1950 | Wettlaufer . |
| 2,574,945 * | 11/1951 | Werner . |
| 2,688,960 | 9/1954 | Fischer et al. . |
| 2,742,036 | 4/1956 | Montesano . |
| 2,917,043 * | 12/1959 | Murphy . |
| 3,019,785 * | 2/1962 | Eiden . |
| 3,310,050 * | 3/1967 | Goldfarb . |
| 3,626,934 | 12/1971 | Andis . |
| 3,799,154 | 3/1974 | Knop . |
| 3,811,430 | 5/1974 | Kawakami . |
| 3,872,526 | 3/1975 | Betts . |
| 3,976,056 | 8/1976 | Brawn . |
| 3,993,053 | 11/1976 | Grossan . |
| 4,098,266 | 7/1978 | Muchisky et al. . |
| 4,370,602 | 1/1983 | Jones, Jr. et al. . |

(List continued on next page.)

FOREIGN PATENT DOCUMENTS

| | | |
|---|---|---|
| 136 896 a | 2/1967 | (GB) . |
| 173556 | 12/1978 | (HU) . |
| 188676 | 3/1984 | (HU) . |
| 194055 | 5/1984 | (HU) . |

OTHER PUBLICATIONS

Michael D. Levitt, et al., Influence of Shaking on Peritoneal Transfer in Rats, Kidney International, vol. 35 (1989), pp. 1145–1150.

J. Rudoy, et al., Externally Applied Abdominal Vibration as a Method for Improving Efficiency in Peritoneal Dialysis, Nephron. 46: 364–366 (1987).

Nippon, et al., Effect of Direct Pulsatile Peritoneal Dialysis on Peritoneal Permeability and Lymphatic Absorption in the Rat, Dept. Of Urology, Kitasato Univ., School of Med., Kanagawa, Japan, Jan. 1995; 37(1):24–8 (abst).

Patent Abstracts of Japan, vol. 016, No. 369 (C–0972), Aug. 10 1992; & JP 04 117964, Apr. 17, 1992.

Primary Examiner—Mark Bockelman
(74) Attorney, Agent, or Firm—Helfgott & Karas, PC (57) ABSTRACT

An appliance to enhance the rate of removal of solutes during a peritoneal dialysis treatment of a subject, includes a holder to be applied to the subject, and a vibrator device, preferably two such devices, carried by the holder at a location to engage the front side of the subject's abdomen and to apply mechanical vibrations thereto at a frequency of 1–15 Hz, and an amplitude of 1–20 mm, particularly surprising results having been obtained at a frequency of 2–6 Hz, and an amplitude of 5–10 mm.

5 Claims, 8 Drawing Sheets

U.S. PATENT DOCUMENTS

| | | |
|---|---|---|
| 4,430,992 | 2/1984 | Christ . |
| 4,597,384 | 7/1986 | Whitney . |
| 4,732,140 | 3/1988 | Stoffregen . |
| 4,788,968 | 12/1988 | Rudashevsky et al. . |
| 4,827,914 | 5/1989 | Kamazawa . |
| 4,846,157 | 7/1989 | Sears . |
| 4,865,020 | 9/1989 | Bullard . |
| 4,883,462 | 11/1989 | Williamson et al. . |
| 4,887,594 | 12/1989 | Siegel . |
| 4,911,149 | 3/1990 | Borodulin et al. . |
| 5,025,781 | 6/1991 | Ferrari . |
| 5,103,808 | 4/1992 | Iams et al. . |
| 5,167,226 | 12/1992 | Laroche et al. . |
| 5,174,281 | 12/1992 | Lee . |
| 5,181,504 | 1/1993 | Ono et al. . |
| 5,300,095 | 4/1994 | Salazar . |
| 5,334,131 | 8/1994 | Omandam et al. . |
| 5,374,238 | 12/1994 | Xiao . |
| 5,383,842 | 1/1995 | Bertini . |
| 5,848,980 * | 12/1998 | Demerais . |

* cited by examiner

VIBRATOR APPLIANCE PARTICULARLY USEFUL FOR DIALYSIS

FIELD AND BACKGROUND OF THE INVENTION

The present invention relates to a vibrator appliance, and particularly to one useful for a peritoneal dialysis (PD) treatment. The invention also relates to a dialysis method and particularly to one utilizing the novel vibrator appliance.

Peritoneal dialysis (PD) is a medical treatment administered when there is insufficient functioning of the kidneys. It is performed by inserting a sterile plastic catheter into the abdominal cavity of the subject and instilling a dialysate solution to irrigate the peritoneum such that solutes transfer across the peritoneal membrane into the dialysate solution from the blood in the mesentery capillary network. This treatment does not require a machine, such as in hemodialysis, but does require much longer periods of time in order to achieve solute removal comparable to that of intermittent hemodialysis. Such a treatment is commonly performed in an ambulatory manner as a CAPD (Continuous Ambulatory Peritoneal Dialysis) treatment.

CAPD is usually performed in four 6-hour sessions during each 24-hour period. In each session, the dialysate solution is instilled into the abdominal cavity of the subject and permitted to dwell therein for a period of six hours, following which the dialysate solution is drained, and a fresh dialysate solution is instilled. This relatively large number of sessions greatly disturbs the daily routine of the subject. It also increases the risk of infection.

Various studies have been conducted on the application of mechanical vibrations for improving the efficiency of waste removal by PD (peritoneal dialysis); see *J. Rudoy et al.* Nephron 46:364–366 (1987); *Levitt et al.* Kidney International, Vol. 35, pp. 1145–1150 (1989); and Utsunomia-T et al., *Nippon-Jinzo-Gakkai-Shi;* 1995 Jan; 37(1):24-8. The Rudoy et al. publication (1987) describes an improvement in peritoneal transfer on human subjects when subjected to mechanical vibrations at a frequency of 24 Hz by a vibrator held by the patient perpendicular to the patient's abdomen; the Levitt et al. publication (1989) describes studies of the effects produced on the rate of peritoneal transfer in rats by shaking the rats; and the Japanese publication (1995) describes studies on the rate of peritoneal transfer in rats by vibrating the abdominal wall at the rate of 80 Hz.

OBJECTS AND BRIEF SUBJECT OF THE INVENTION

Objects of the present invention are to provide a vibrator appliance particularly useful in peritoneal dialysis, and also an improved method of peritoneal dialysis. The apparatus and method of the present invention are particularly useful for CAPD, but may also be used for other PD treatments, such as APD (Automated Peritoneal Dialysis), and CCPD (Continuous Cycling Peritoneal Dialysis) usually administered at home during the nighttime.

According to one aspect of the present invention, there is provided an appliance to enhance the rate of removal of solutes during a peritoneal dialysis treatment of a subject, comprising: a holder to be applied to the subject; and at least one vibrator device carried by the holder at a location thereof to engage the subject's abdomen and to apply localized, inwardly-directed mechanical vibrations thereto at a frequency of 1–15 Hz.

As will be described more particularly below, surprisingly good results were produced when the vibrator device applies the mechanical vibrations at a frequency of 2–6 Hz, In the preferred embodiments of the invention described below, there are two vibrator devices carried by the holder at locations to engage the opposite sides of the subject's abdomen and oriented to apply inwardly-directed mechanical vibrations towards the central region of the subject's abdominal cavity.

According to another aspect of the invention, there is provided a method of administering a peritoneal dialysis treatment to a subject comprising a vibration session including: instilling a dialysate solution into the peritoneal cavity of the subject; applying external localized mechanical vibrations to the front side of the abdomen of the subject at a frequency of 1–15 Hz and an amplitude of 1–20 mm; and draining the dialysate solution from the subject's abdominal cavity. As indicated above, and as will be more fully described below, surprisingly good results were obtained when the mechanical vibrations were applied, at a frequency of 2–6 Hz and at a amplitude of 5–10 mm, especially when two vibrator heads were used engaging the front side of the subject's abdomen on opposite sides of its center line and oriented to direct mechanical vibrations to the central region of the subject's abdominal cavity.

Thus, it was found that applying the vibrations at a frequency of over 15 Hz did not permit the vibrations to propagate deeply into the body cavity, and therefore the 24 Hz frequency mentioned in the J. Rudoy et al. publication cited above only produced a limited improvement in the peritoneal dialysis treatment. It was also found that applying the vibrations at a frequency of less than 1 Hz also produced very limited benefits. Surprisingly good results were found in the frequency range of 2–6 Hz, which produced an improvement of up to 150% in the solute removal rate, as compared to an improvement of about 30–40% when applying the mechanical vibrations at a frequency of 24 Hz as described in the J. Rudoy et al. publication.

The optimum rate, preferably within the 2–6 Hz range, can be determined emperically for each subject, according to the size, build and weight of the subject.

The vibrational amplitudes are preferably in the range of 1–20 mm, best results having been obtained with amplitudes of 5–10 mm. These amplitudes are inversely related to the frequency; that is, at the lower end of the above frequency range the vibrational amplitudes would be at the higher end of the amplitude range, and vice versa. Preferably, the combination of amplitude and frequency should be just below the level producing significant pain or discomfort to the subject, e.g., at the second limit of ISO Standard 2631.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
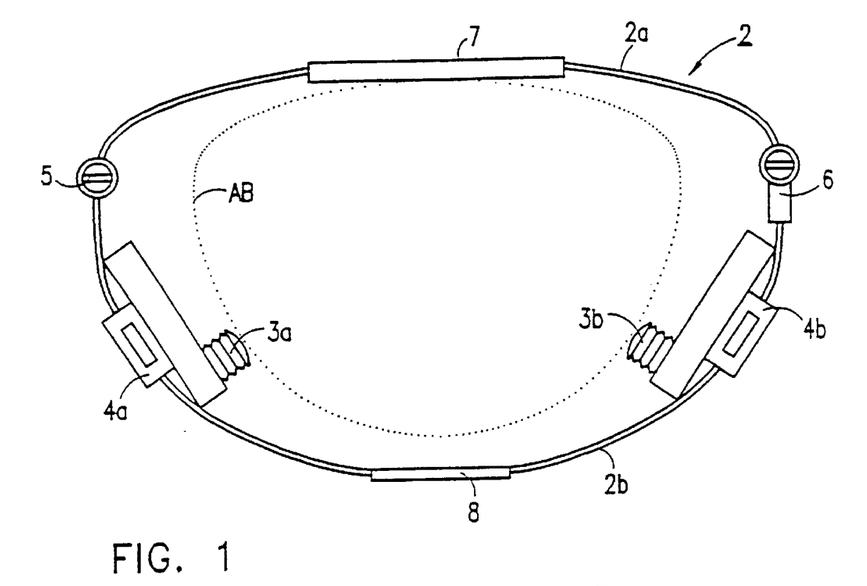
FIG. 1 illustrates one type of vibrator appliance constructed in accordance with the present invention utilizing an electrically-actuated vibrator.

The vibrator appliance illustrated in FIG. 1 includes a holder 2 of a closed loop configuration to enclose the wearer's abdomen, indicated by broken lines AB. Holder 2 carries two vibrators 3a, 3b, each slidably mounted on the holder by a slide 4a, 4b, to enable each vibrator to be located so as to apply mechanical vibrations to opposite sides of the abdomen of the subject.

Holder 2 includes a back frame 2a, and a front frame 2b mounting the two vibrators 3a, 3b. One end of front frame 2b is pivotal, by hinge 5, to the respective end of the back frame 2a for opening and closing the holder. The opposite end of front frame 2b is lockable to the respective end of the back frame 2a by a lock, schematically shown at 6, for locking the holder in its closed condition. Both the back frame 2a and the front frame 2b include width-adjusting means, as shown at 7 and 8, respectively, for adjusting the size of the holder to fit persons of different sizes. Such width adjustment means 7, 8 may be of any conventional construction, such as slidable or telescoping sections in the respective frames.

Holder 2 may be worn by the subject in a self-supporting manner with the two vibrators 3a, 3b engaging the front side of the subject's abdomen, on opposite sides of its center line. Thus, when the two vibrators 3a, 3b are energized, they produce mechanical vibrations which are inwardly-directed towards the center region of the subject's abdominal cavity.

Figures 2, 3:
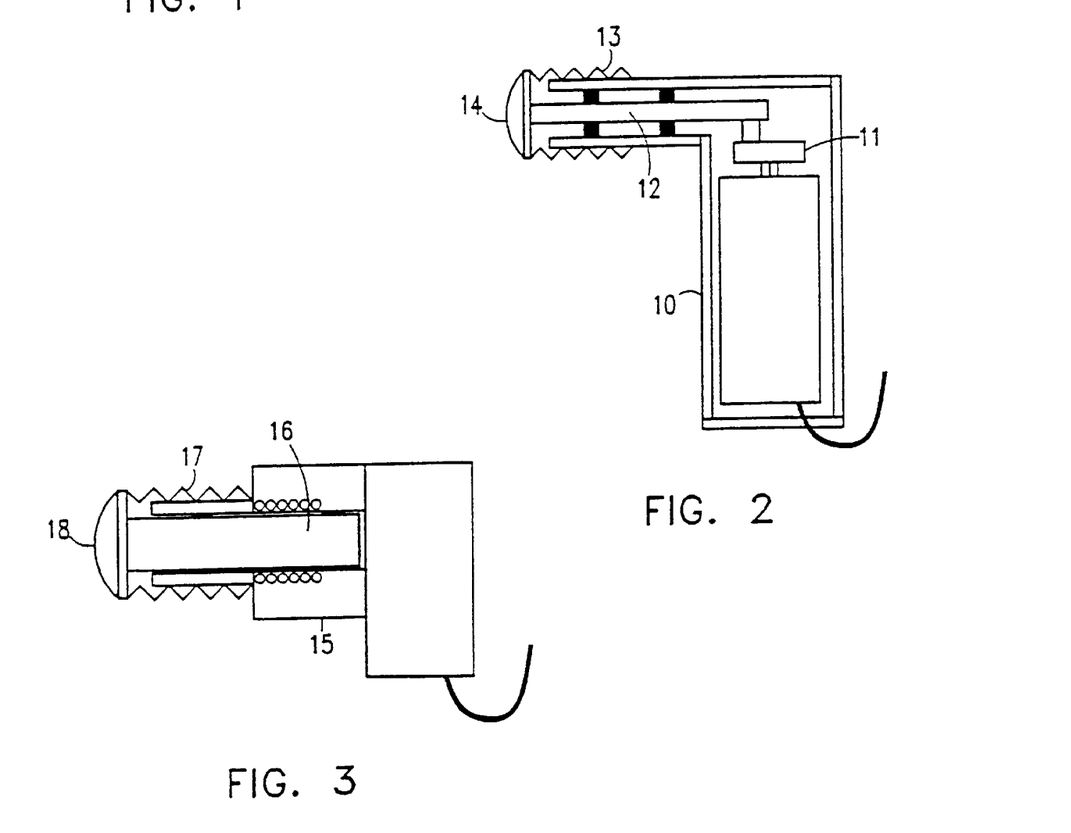
FIG. 2 illustrates a rotary-motor type vibrator that may be used in the appliance of FIG. 1.
FIG. 3 illustrates a solenoid-type of vibrator that may be used in the appliance of FIG. 1.

In the embodiment illustrated in FIG. 1, the two vibrators 3a, 3b, are electrically-driven. FIG. 2 illustrates one example of such a vibrator, in the form of a rotary motor 10 rotating a disc 11 eccentrically mounting an arm 12 enclosed within a bellows 13 having a head 14 engageable with the user's abdomen such that energization of motor 10 reciprocates the eccentric arm 12 and its head 14 to apply mechanical vibrations to the wearer's abdomen. FIG. 3 ilustrates another example of vibrator, in the form of a solenoid 15 reciprocating an armature 16 enclosed within a bellows 17 and having a head 18 engaging the wearer's abdomen to apply mechanical vibrations thereto upon the energization of the solenoid. A still further example, including an electric motor driving eccentric weights is described below with reference to FIG. 7. The displacements of the vibrations may be adjusted or changed by changing the eccentricity of arm 12 in the appliance of FIG. 2, the current through the solenoid 15 in the appliance of FIG. 3, and the weights in the appliance of FIG. 7.

The use of the vibrator appliance illustrated in FIGS. 1–3 has been found to enable a CAPD treatment to be divided into two 12-hour sessions, rather than four 6-hour sessions as in the conventional CAPD treatment. Following is one example of such a two-session treatment:

In each session, dialysate solution is instilled into the abdominal cavity of the subject, and the two vibrators 3a, 3b are driven to cause them to apply mechanical vibrations to the abdomen, at a frequency of 1–15 Hz, at a vibrational amplitude of 1–20 mm, and for a period of 15–60 minutes. After this dwell period, the dialysate solution is drained from the suject; fresh dialysate solution is instilled and permitted to dwell in the subject for the remaining 12-hour period of that session; and the dialysate solution is then drained. This completes one 12-hour session, whereupon the next 12-hour session is started, and the foregoing sequence of steps is repeated. As indicated earlier, when the frequency was 2–6 Hz, the vibrational amplitude was 5–10 mm, and the dwell period was from about 30–40 minutes, surprisingly improved results were obtained producing an improvement of up to about 150%, as compared to a 30–40% improvement mentioned in the above-cited J. Rudoy et al. publication using 24 Hz vibrations.

These improved results enabled the normal four session CAPD treatment to be reduced to two sessions, each session involving e.g., a 40-minute dwell period accompanied by the vibrations, and immediately followed by, e.g., an 11-hour 20-minute dwell period not accompanied by vibrations. Thus, the 40-minute dwell period accompanied by vibrations was found to remove substantially the same amount of solutes as a normal 6-hour session in the conventional CAPD treatment. Such a 2-session regimen is not only much more convenient and substantially less disruptive of the daily routine of the patient than the usual 4-session regimen, but also substantially reduces the possibility of infection.

The two vibrators may be operated at the same constant frequency, at different frequencies, or with changing frequencies. They may be operated in the same phase or in different phases. One or both vibrators may also be operated in a continuously changing phase angle. Best results were obtained when both vibrators were operated within the range of 2–4.5 Hz, with one vibrator operating at a slightly different frequency than the other (such as 2.5 Hz and 2.6 Hz, respectively) to produce alternating in-phase and out-of-phase movements of the subject's abdomen. The subject may be in a sitting, lying or standing position during the first part of each session when the vibrations are applied, but best results were obtained when the subject was in a sitting or supine position.

Figure 4:
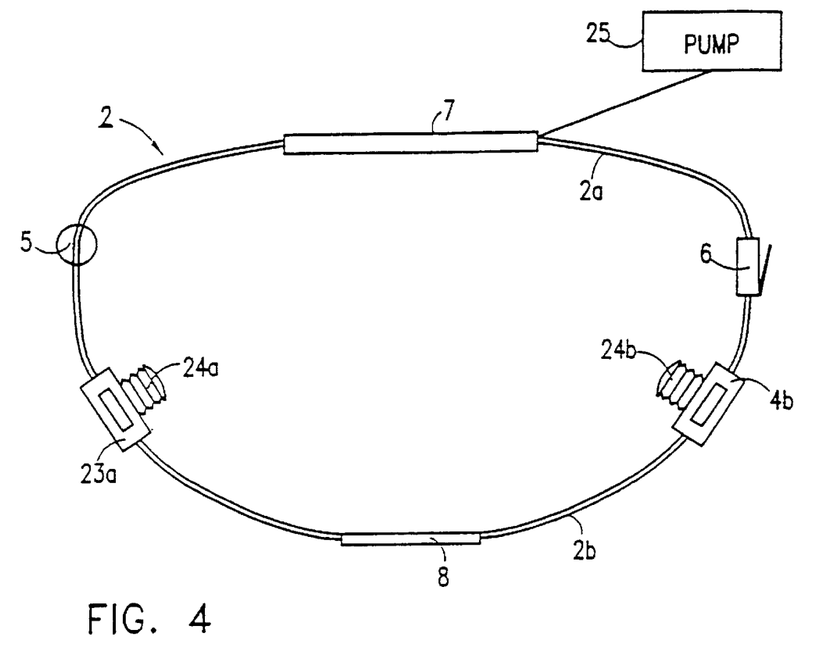
FIG. 4 illustrates a piston-type vibrator appliance constructed in accordance with the present invention.

FIG. 4 illustrates a vibrator appliance, similar to that of FIG. 1 except that the vibrators, therein designated 23a, 23b, respectively, are in the form of fluid pistons movable within cylinders to apply the vibrations to the wearer's abdomen. In FIG. 4, each of the vibrators 23a, 23b is shown as including a bellows 24a, 24b, enclosing the piston of the respective vibrator. The pistons in vibrators 23a, 23b, may be operated pneumatically or hydraulically. FIG. 4 schematically illustrates a pump or compressor 25 for operating these pistons. In all other respects, the vibrator appliance illustrated in FIG. 4 is constructed and operates in substantially the same manner as described above with respect to FIG. 1, and therefore the corresponding elements of the appliance are identified by the same reference numerals to faciliate understanding.

Figure 5:
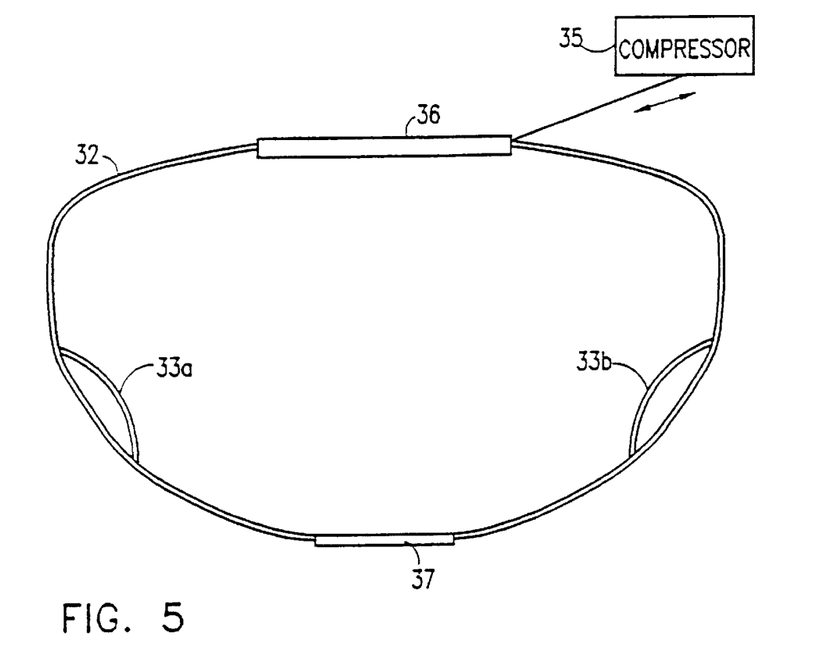
FIG. 5 illustrates an air-bag type vibratory appliance constructed in accordance with the present invention.

FIG. 5 illustrates another form of vibrator appliance wherein the holder is in the form of a belt 32 to enclose the subject, and the vibrators are in the form of inflatable air bags 33a, 33b carried by the belt on the opposite sides of the wearer's abdomen. The air bags 33a, 33b are inflatable and deflatable at the desired frequency by a compressor 35.

Belt 32 includes a stiff back 36 and a front adjustment 37 for adjusting the belt to fit persons of different sizes. While FIG. 5 illustrates a compressor 35 for both vibrators, it will be appreciated each vibrator could be provided with its own compressor particularly if they are to be operated at different frequencies or phases. The same apllies with respect ot the appliance of FIG. 4.

Figure 6:
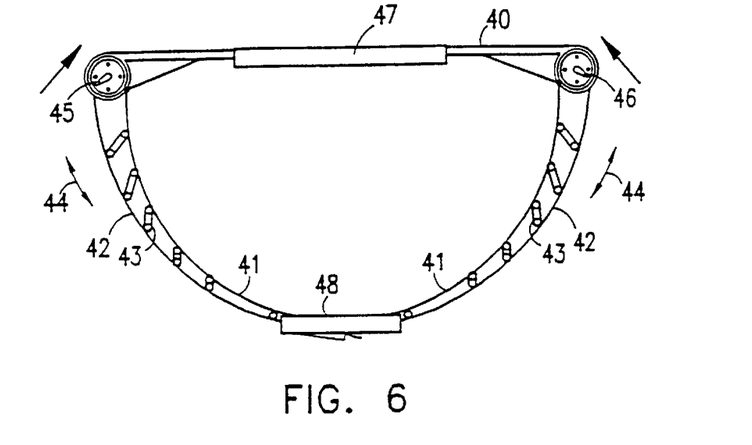
FIG. 6 illustrates a moving-belt type vibrator appliance constructed in accordance with the present invention.

FIG. 6 illustrates a further vibrator appliance, in which the holder includes a frame 40 to engage the back of the wearer, a first belt 41 to be applied around the wearer, and a second belt 42 to be applied around the first belt 41. This appliance also includes two vibrators applying mechanical vibrations to the opposite sides of the wearer's abdomen. In this case, each vibrator includes a plurality of plates 43 pivotally mounted at one end to the inner belt 41, and at the opposite end to the outer belt 42. The arrangement is such that when belt 42 is reciprocated, in the direction of arrows 44, the two groups of plates 43 are pivotted through a plurality of positions from 0° to 180°, and during such pivotal movements of these plates, they apply mechanical vibrations to the wearer's abdomen. Thus, when the plates are 0° to the two belts 41, 42, the vibrational amplitude is zero, but as the plates move to positions of 90° to the two belts, they apply mechanical vibrations to the wearer's abdomen at amplitudes corresponding to the widths of the plates.

Each vibrator thus includes one group of plates 43 pivotally mounted between the two belts 41, 42. The width of each plate 43 decreases from the rear side to the front side of the respective vibrator so that the vibrational amplitudes are correspondingly decreased from the rear side towards the front side of the vibrator.

FIG. 6 schematically illustrates the front belt 42 as being reciprocated by a pair of motors 45, 46, at the opposite ends of the rear frame 40. An adjustment 47 for the rear frame 40, and an adjustment 48 for the two belts 41, 42, enable the appliance to fit persons of different sizes.

Figure 7:
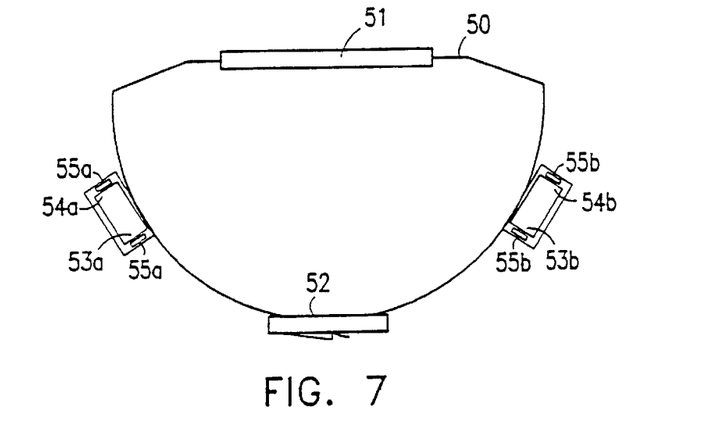
FIG. 7 illustrates another vibratory appliance including a belt supporting two electric motors rotating eccentric weights.

FIG. 7 illustrates another appliance, including a belt 50 having a back adjustment 51 and a front adjustment 52 to enable the appliance to be fitted to different size individuals. Belt 50 carries a pair of vibrators 53a, 53b on its opposite sides to engage the opposite sides of the wearer's abdomen. Each vibrator 53a, 53b includes an electric motor 54a, 54b, driving a pair of eccentric weights 55a, 55b which, upon energization of the respective motors, apply mechanical vibrations to the wearer's abdomen.

Figure 8:
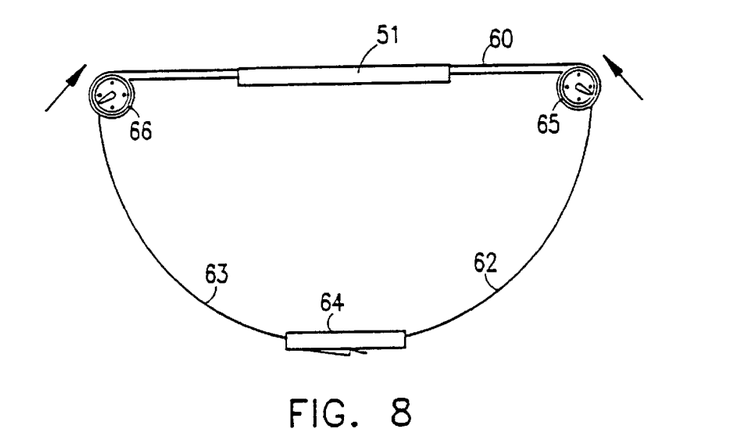
FIG. 8 illustrates a further appliance in which the vibrations are effected by a pair of motors which cyclically tension and relax a belt applied to the wearer's abdomen.

FIG. 8 illustrates an even more simplified construction, including a back frame 60 having an adjustment 61, and front belts 62, 63 having a front adjustment 64. The back frame 60 carries a pair of electric motors 65, 66 engaging the opposite ends of belts 62, 63 such that energization of the electric motors cyclically tensions and relaxes the belts to cause them to apply mechanical vibrations to the opposite sides of the wearer's abdomen engaged by the belts.

Figure 9:
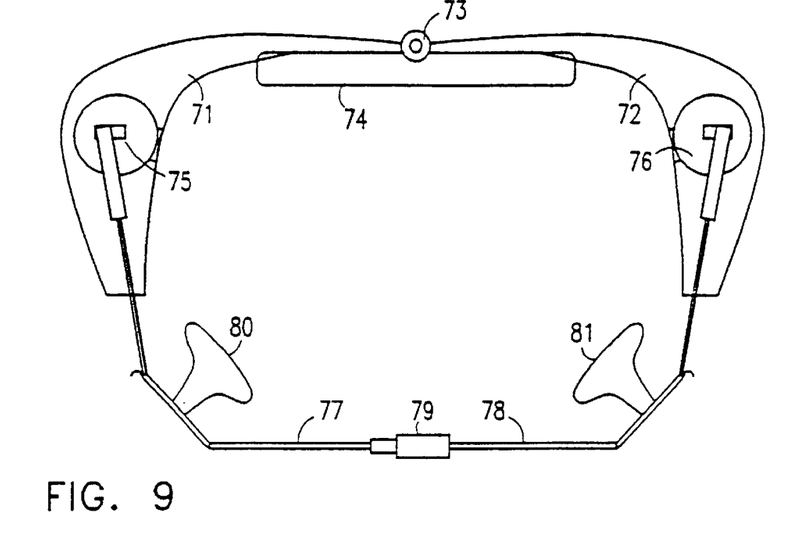
FIG. 9 is a plan view illustrating a further type of appliance constructed in accordance with the present invention.
Figure 10:
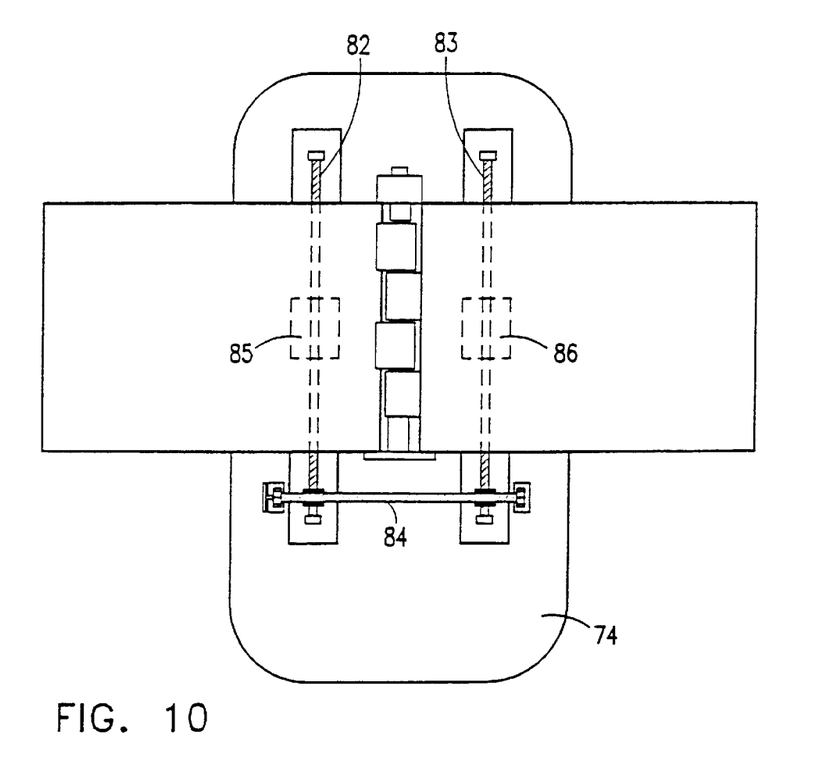
FIG. 10 is a rear view of the appliance of FIG. 9.

FIGS. 9 and 10 illustrate another appliance 70 also including a holder in the form of a loop to be worn by the subject in a self-supporting manner. In this case, the appliance includes two base members 71, 72 coupled together by a hinge 73 and mounted to a stiff or rigid back plate 74 adapted to engage the back of the subject. The base, members 71, 72 mount electrical motors 75, 76 which are eccentrically coupled to one end of a pair of flexible belts 77, 78 adapted to engage the front side of the subject's abdomen. The opposite ends of belts 77, 78 are coupled together by a locking device or buckle 79.

A pair of vibrator heads 80, 81 are carried by the two belts 77, 78. Heads 80, 81 extend inwardly of the loop to contact the front side of the subject's abdomen on opposite sides of its center line and are oriented towards the central region of the subject's abdominal cavity. Thus, when the two electrical motors 75, 76 are energized, their eccentric connections to the flexible belt 77, 78 cyclically tension and relax the belts causing the vibrator heads 80, 81 to apply mechanical vibrations directed to the central region of the subject's abdominal cavity.

The front buckle or lock 79 is adjustable to permit the diameter of the loop to be adjusted according to the size of the subject. The two vibrator heads 80, 81 are slidable on the belts 77, 78 to permit them to be optimally positioned in order to direct the mechanical vibrations to the central region of the subject's abdominal cavity. The two hinged base members 71, 72 may also be adjustable on the back plate 74. Thus, as shown in FIG. 10, the back plate 74 carries two parallel screws 82, 83 rotate together by another screw 84. Screws 82, 83 on the back plate 74 are received within nuts 85, 86 on the two base members 71, 72, such that rotation of the two screws 82, 83 by the common screw 84 moves the two base members 71, 72 up or down according to the direction of rotation of screws 84.

Figure 11:
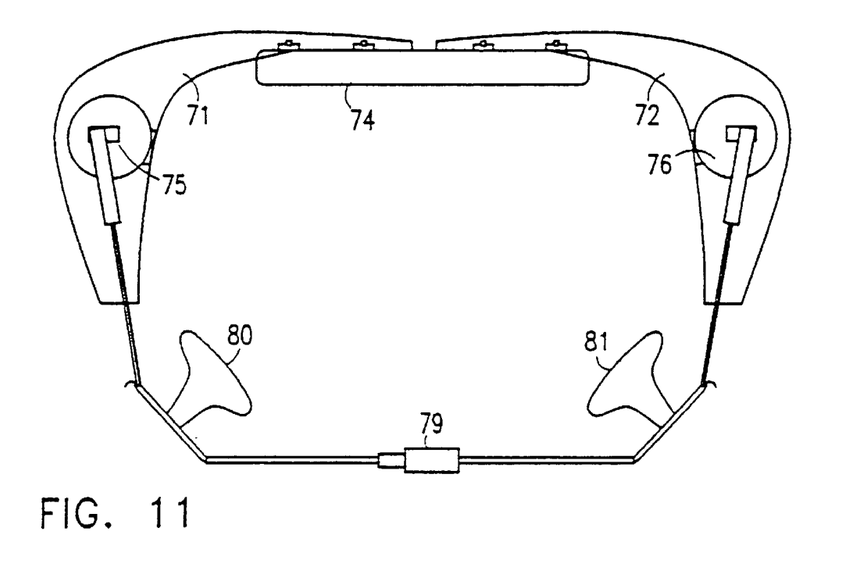
FIG. 11 is a plan view illustrating a still further appliance constructed in accordance with the present invention.
Figure 12:
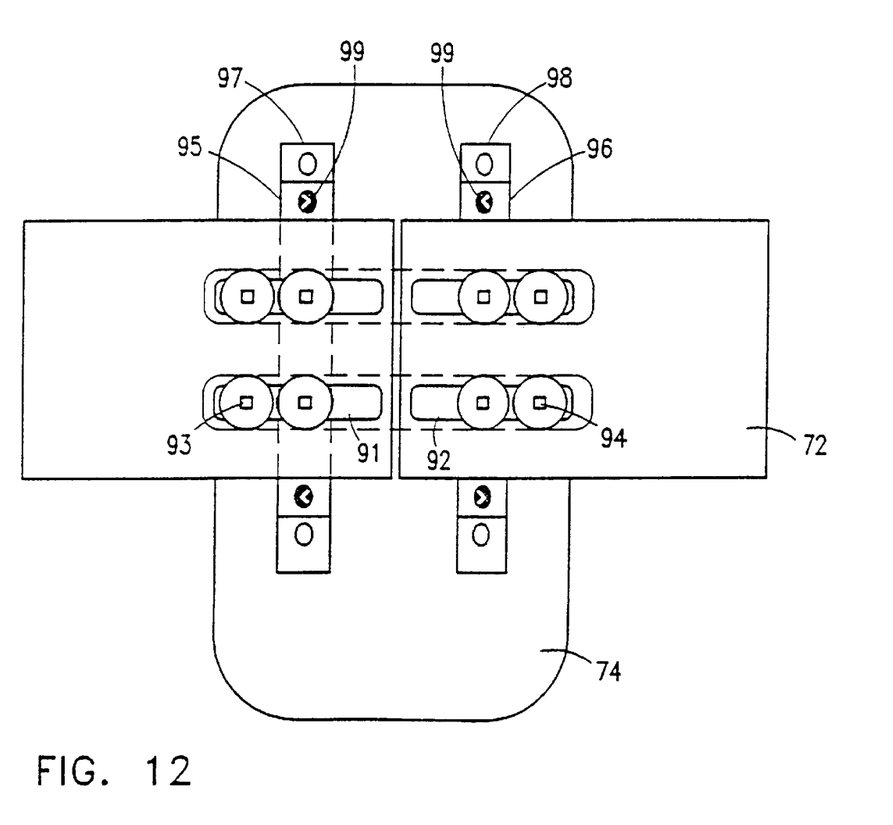
FIG. 12 is a rear view of the appliance of FIG. 11.

FIGS. 11 and 12 illustrate a similar appliance as in FIGS. 9 and 10, and therefore the same reference numerals have been used for the same parts. In the appliance of FIGS. 11 and 12, however, the ends of the two base members 71, 72 are not hinged together, but rather are formed with parallel slots 91, 92 receiving threaded pins 93, 94. In addition, each base member 71, 72 has secured thereto a transverse rigid strip 95, 96 adapted to be received within grooves 97, 98 formed in the back plate 74. Strips 95, 96 carried by the base members 71, 71, and grooves 97, 98 in the back plate 74, are formed with a plurality of openings extending along the length of the strips and grooves, respectively, adapted to selectively receive threaded pins 99. Thus, by threading pins 99 in selected openings in the strips 95, 96, and grooves 97, 98, the position of the base members 71, 72 may be adjusted along the length of the back plate; and by tightening the threaded pins 93, 94 in their respective slots 91, 92, the diameter of the appliance may be adjusted to fit different sized persons.

Figure 13:
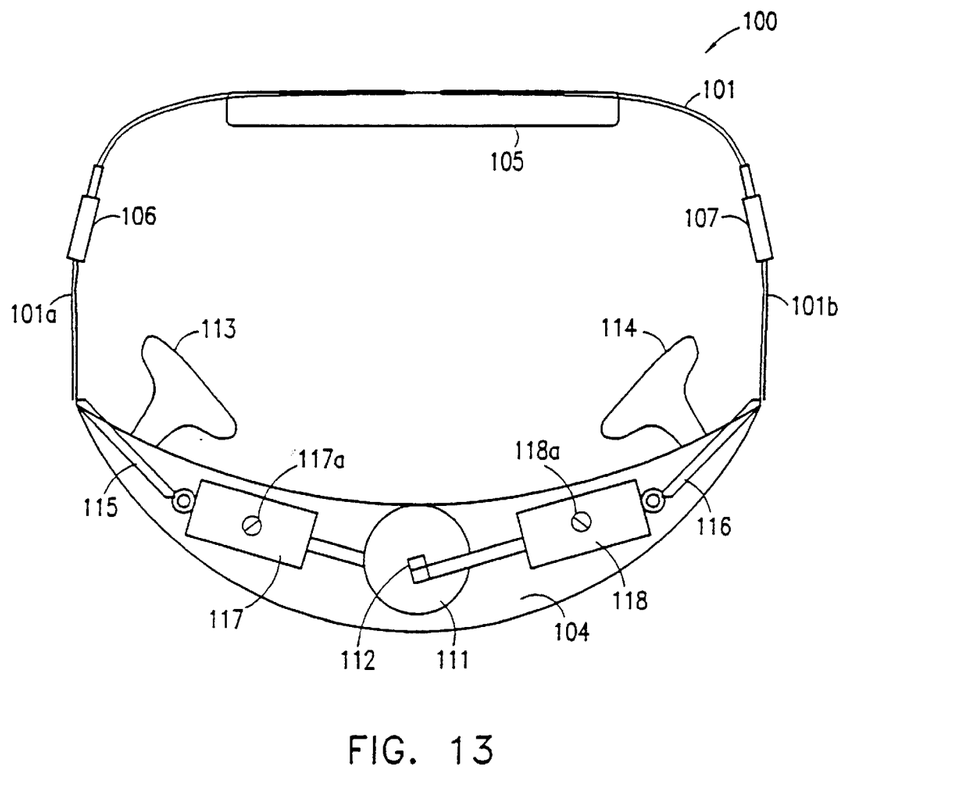
FIG. 13 is a plan view of a still further appliance constructed in accordance with the present invention.
Figure 14:
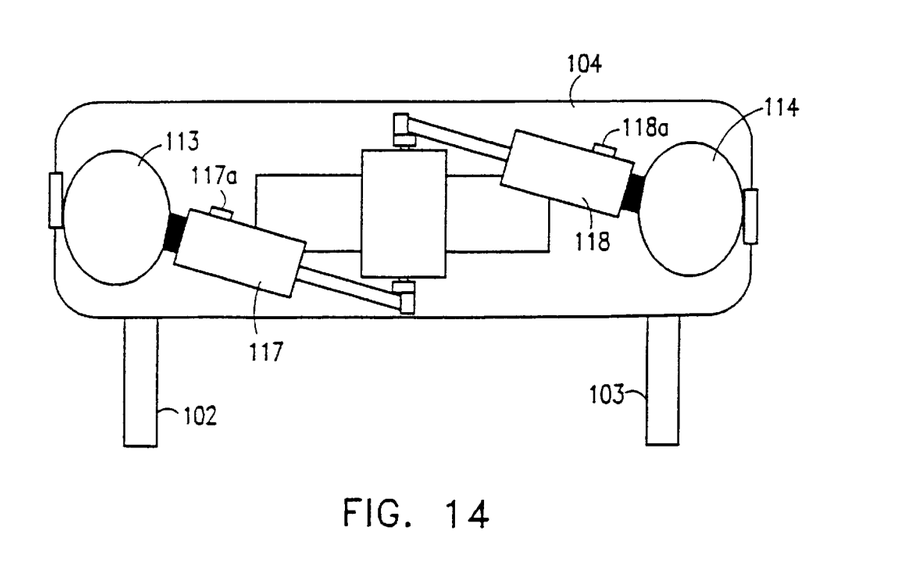
FIG. 14 is a front view of the appliance of FIG. 13.

FIGS. 13 and 14 illustrate another appliance 100 which includes a loop enabling the appliance to be worn by the user in a self-supporting manner, but further includes a pair of shoulder harnesses 102, 103 to aid the loop in supporting the appliance on the subject.

The appliance 100 illustrated in FIGS. 13 and 14 includes a base member 104 at the front of the appliance, i.e., to engage the front side of the subject's abdomen, and a back plate 105 at the opposite side of the appliance to engage the subject's back. The base member 104 is connected to the back plate 105 by a pair of flexible belts 101a, 101b, to thereby define the closed loop 101 enabling the appliance to be worn by the subject. Each of the flexible belts includes a locking member or buckle 106, 107 of the type which permits the lenght of the belt to be adjusted and locked, to thereby enable the appliance to fit different sized persons.

Base member 104 at the front side of the appliance carries an electrical motor 111 having an output shaft 112 eccentrically coupled at its opposite ends to a pair of shaped vibrator heads 113, 114 carried by plates 115, 116 pivotally mounted to he base member 104. Each of the eccentric couplings between the motor output shaft 112 and the vibrator heads 113, 114 includes a dashpot device 117, 118 pivotally mounted to plates 115, 116. Each dashpot device 117, 118 includes an adjustment, indicated by screws 117a, 118a, which permits manual adjustment of the retarding action of the respective dashpot. The retarding action of each dashpot may also be remotely adjusted via electrical or hydraulic means. These adjustments may be used not only for adjusting the cushioning forces applied by the vibrator heads 113, 114 against the subject's abdomen, but also for changing the relative phases of the forces so applied, upon rotation of the electrical motor 111.

Figure 15:
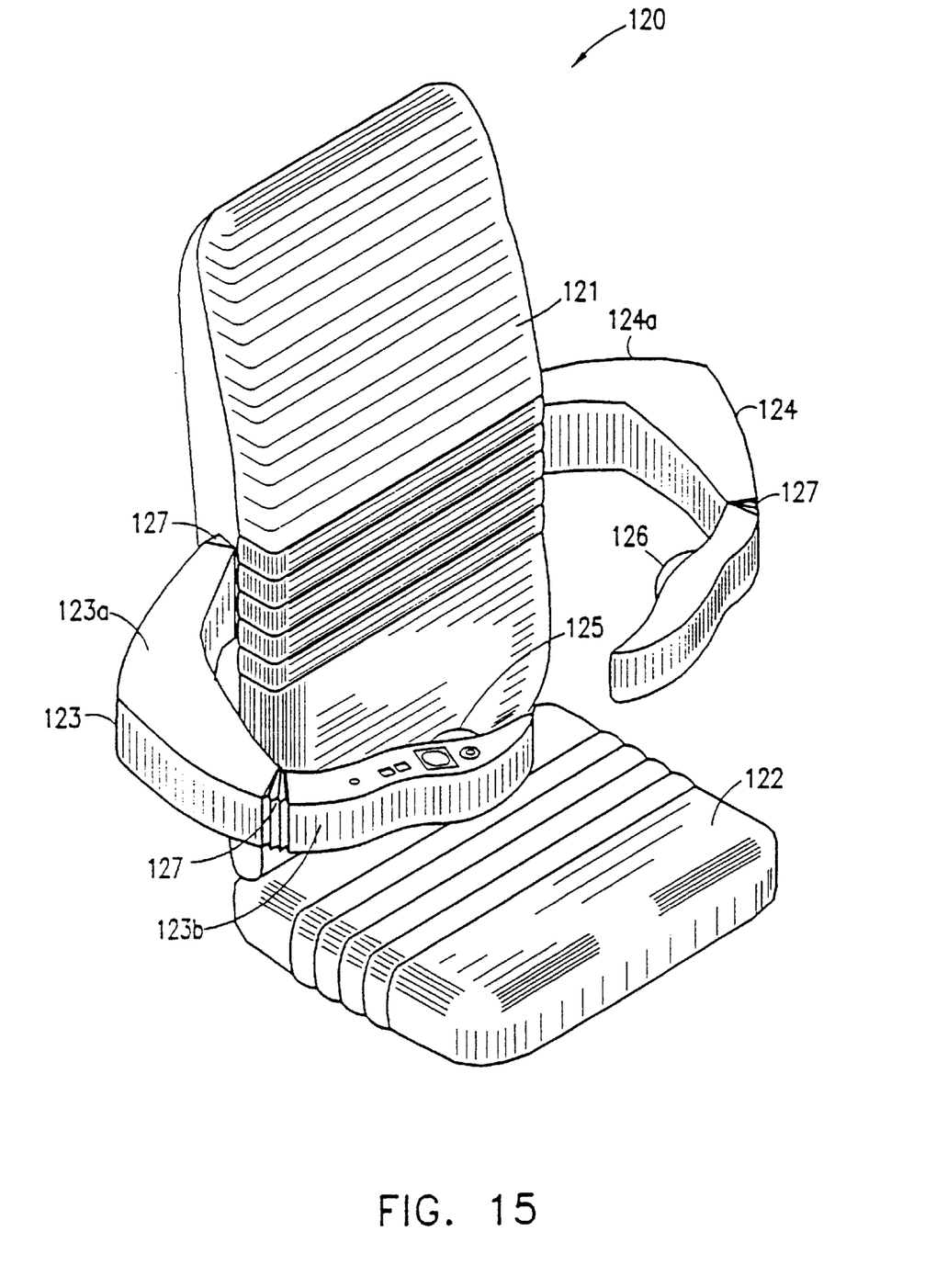
FIG. 15 is an artist's view of one form of vibrator appliance constructed in accordance with the present invention.

FIG. 15 illustrates the external appearance of a vibrator appliance 120 constructed in accordance with the present invention. The appliance includes a backrest 121, a seat 122 and a pair of arms 123, 124, each having a rear section 123a, 124a, pivotally mounted to the backrest 121, and a front section 123b, 124b, carrying a vibrator head 125, 126 to engage the front side of the subject's abdomen. The rear arm sections 123a, 124a are pivotally mounted to the backrest 121, as schematically indicated by integral hinge 127, and may be fixed in any pivotted position by any suitable means such as a screw and nut arrangement (not shown). Similarly, the front arm sections 123b, 124b are pivotally mounted to their respective rear arm sections 123a, 123b, as indicated by integral hinges 127, and may also be fixed in any pivotted position, to thereby enable the appliance to be used with respect to persons of different sizes. The vibrator heads 125, 126 carried by the front arm sections 123b, 124b, may be driven electrically, hydraulically, or pneumatically, according to any of the above-described arrangements.

Figure 16:
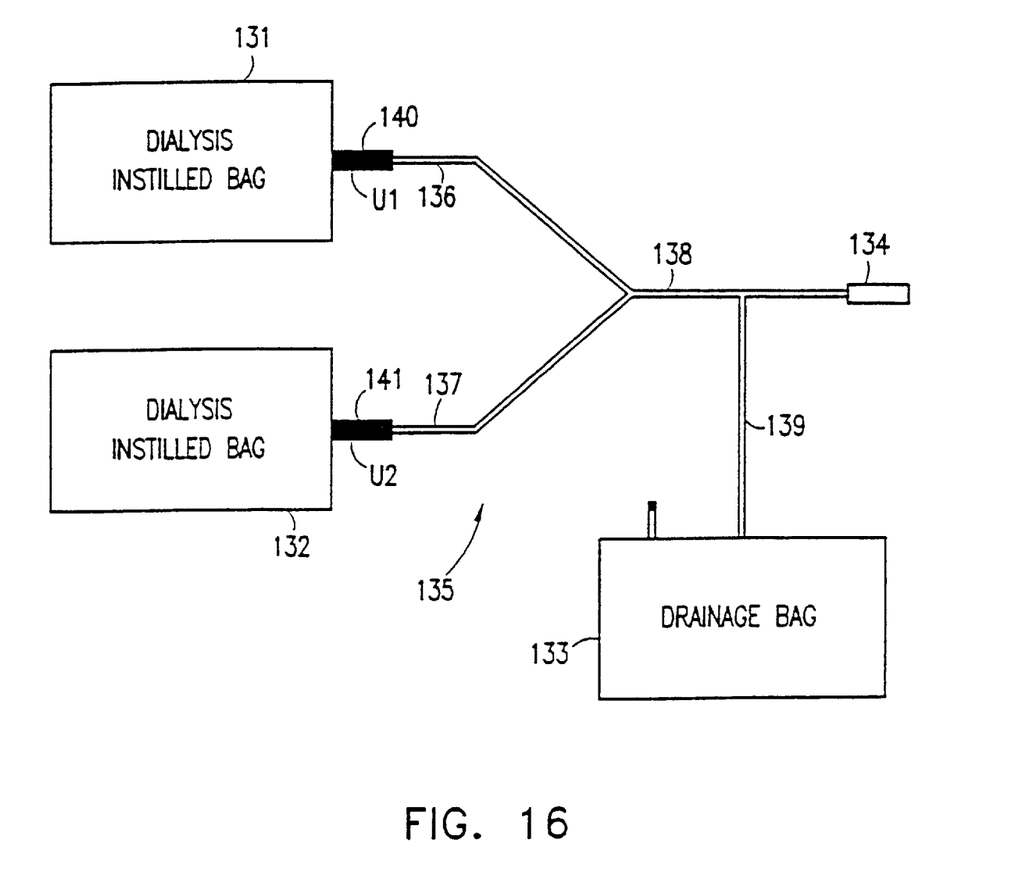
FIG. 16 illustrates a dialysis set particularly useful with the appliance and method of the present invention.

FIG. 16 illustrates a dialysis set particularly useful with respect to the above-described appliance. The illustrated set includes two supply bags 131, 132 for containing fresh dialysis solution, and a drainage bag 133 to receive the solution after drained from the subject. The three bags are connected to a connector 134 for the dialysis catheter (not shown) by tubing generally designated 135. Tubing 135 includes two tubes 136, 137, connected at one of their ends to the respective supply bag 131, 132, and at their opposite ends to a third tube 138 leading to the catheter connector 134. Tube 138 is connected to a fourth tube 139 leading to the drainage bag 133.

Each tube 136, 137 includes a valve 140, 141 which is normally closed, but which can be manipulated to open and thereby to permit the respective supply bag 131, 132 to instill its fluid to the patient via the catheter connected to connector 134. Valves 140, 141 may be breakaway valves which are normally closed, but which may be manually broken-away to open the valve.

In use of the dialysis set illustrated in FIG. 16, the two supply bags 131, 132 would be mounted at a higher elevation than the catheter connector 134, and the drainage bag 133 would be mounted at a lower elevation than the catheter connector. In addition, an external clamp (not shown) would be applied to tube 139 to prevent the dialysis solution from passing to the drainage bag 133 during instillation phase. With a clamp thus applied to tube 139, valve 140 would be manipulated to open, thereby permitting the fluid to flow by gravity from supply bag 131 via the catheter into the abdominal cavity, whereupon the vibrator appliance would be energized to enhance the rate of solute removal. After the appropriate dwell time, the clamp would be removed from tube 139 to permit the solution to drain into the drainage bag 133, whereupon the clamp would then be reapplied to tube 139 and valve 141 of supply bag 132 would be opened to permit the solution in that bag to flow by gravity into the abdominal cavity of the subject.

The dialysis set illustrated in FIG. 16 may thus be connected to the patient's catheter during two successive exchanges, thereby substantially reducing the possibility of an infection and also reducing the disruption to the patient's daily routine.

Generally speaking, it was found that a 40-minute dialysate treatment accompanied by mechanical vibrations applied in any of the above-described appliances effects about the same solute transfer as a 6-hour dialysate treatment not accompanied by mechanical vibrations. Accordingly, such an appliance permits various treatments to be applied, according to the nature of each case and the convenience of the subject. Following are examples of such treatments:

(1) Each each 24-hour day is divided into two 12-hour periods, each period including a vibration session for 15–60 minutes, and a non-vibration session with fresh dialysate solution for the remainder of the period.

(2) Each 24-hour day includes four vibration sessions of 15–60 minutes each, spaced about six hours apart.

(3) Each 24-hour day is divided into four 6-hour periods, at least one of these periods including a vibration session for 15–60 minutes, and a non-vibration session with fresh dialysate solution for the remainder of the period, each of the remaining periods being a non-vibration session with fresh dialysate.

(4) Each 24-hour day includes a vibration session for 15–60 minutes, a non-vibration session with fresh dialysate solution for 10–11.5 hours, and another vibration session with fresh dialysate for 15–60 minutes.

(5) Each 24-hour day includes six equally-spaced 1–1.5 hours each, each period including instilling fresh dialysate solution for 10–15 minutes, a dwell accompanied by vibrations for 30–60 minutes, and removing the dialysate solution for 15–20 minutes.

In all the above treatments except treatment (4) above, each session (vibrating or non-vibrating) should involve the instillation of 2–2.5 liters of the dialysate fluid. However, in treatment (4) above, since there are a total of only three sessions during the 24-hour day, each session should involve the instillation of about 2.5–3.0 liters of the dialysate fluid.

Each vibration session should be between 15–60 minutes, a 40 minute period having been found to be preferred in most cases. In addition, after each vibration session the dialysate should be drained and fresh dialysate added for the next session.

When the vibrator appliance is used for a continuous 24-hour day (CAPD) treatment, it may be constructed as described above so as to be worn on the user, thereby enabling the user to perform daily routines in the least-disruptive manner. However, when the vibrator appliance is not to be used continuously, it may be incorporated in a self-supporting structure, such as a chair as described above, or a stand or table.

It was further surprisingly found that when the vibrator appliance was operated at the lower frequencies, e.g., 1–3 Hz, it promoted sleep on the part of the wearer. Actually, during clinical experiments, the wearers frequently went to sleep when the appliance was operated at these lower frequencies 1–3 Hz, but immediately awoke when the vibrations were stopped or the frequency was increased to the 2–6 Hz range. The illustrated appliance may therefore be advantageously used also for promoting sleep.

While the invention has been described with respect to several preferred embodiments, it will be appreciated that these are set forth merely for purposes of example, and that many variations may be made. For example, in all the described devices, the two vibrators can be operated at the same frequency but with different phases, at different frequencies, or at progressively changing frequencies. In addition, whereas the above described embodiments include two vibrators engaging opposite sides of the subject's abdomen, a different number of vibrators could be used. Also, the dashpot devices illustrated in FIGS. 13 and 14 may be used with any of the other vibrator devices between the vibrator heads and the respective drives. Many other variations, modifications and applications of the invention will be apparent.

What is claimed is:

1. A method of peritoneal dialysis treatment of a subject comprising the steps of:

causing a vibrator assembly, comprising at least two vibrators, mounted relative to the subject on a vibrator assembly support, to engage a region of the trunk of the subject; and operating the at least two vibrators of said vibrator assembly at frequencies of between 1 and 15 Hz to apply localized inwardly-directed mechanical vibrations thereto while peritoneal dialysis is taking place in the subject's body.

2. A method of peritoneal dialysis treatment of a subject comprising the steps of:

mounting a vibrator assembly, including at least two vibrators, onto a subject;

performing peritoneal dialysis treatment on a subject during a treatment session; and operating the at least two vibrators of said vibrator assembly at frequencies of between 1 and 15 Hz to provide vibrations to the subject for increasing the efficacy of said peritoneal dialysis.

3. Vibrator apparatus for applying vibrations to the abdomen of a subject, comprising;

a chair operative to generally support the body weight of a subject;

at least one arm rest attached to said chair including a first arm portion and a second arm portion adjustably positionable with respect to said first arm portion so as to rest against the abdomen;

a vibrator assembly mounted on said second arm portion of said at least one arm and being positionable relative to said first arm portion to engage an abdominal region of the subject, thereby to apply thereto localized inwardly-directed mechanical.

4. Vibrator apparatus comprising:

a holder to be applied to a subject;

at least one vibrator device carried by said holder at a location thereof to engage the subject's abdomen and to apply localized inwardly-directed mechanical vibrations thereto at a frequency of 1–15 Hz;

wherein said holder comprises:

a first belt dimensioned to enclose the wearer; and a second belt dimensioned to enclose said first belt;

said at least one vibrator device comprising:

a plurality of plates, each pivotably mounted at opposite ends thereof to said first and second belts so as to be pivotal through a plurality of positions from substantially 0 degrees to 180 degrees with respect to said first and second belts; and a drive for reciprocating said second belt with respect to said first belt thereby to oscillate said plurality of plates through said plurality of positions.

5. Vibrator apparatus according to claim 4 and wherein said plurality of plates have at least one dimension of sequentially decreasing extent.

\* \* \* \* \*